United States Patent
Griguol et al.

(10) Patent No.: US 9,017,709 B2
(45) Date of Patent: Apr. 28, 2015

(54) COMPOSITION COMPRISING POLYMERIC, WATER-INSOLUBLE, ANIONIC PARTICLES, PROCESSES AND USES

(75) Inventors: Osvaldo Nicolas Griguol, Cordoba (AR); Dante Miguel Beltramo, Cordoba (AR); Ismael Dario Bianco, Cordoba (AR); Roxana Alasino, Cordoba (AR)

(73) Assignee: Promedon S.A., Cordoba (AR)

( * ) Notice: Subject to any disclaimer, the term of this patent is extended or adjusted under 35 U.S.C. 154(b) by 1016 days.

(21) Appl. No.: 11/990,280

(22) PCT Filed: Aug. 11, 2005

(86) PCT No.: PCT/IB2005/003470
§ 371 (c)(1),
(2), (4) Date: Feb. 27, 2009

(87) PCT Pub. No.: WO2007/017712
PCT Pub. Date: Feb. 15, 2007

(65) Prior Publication Data
US 2009/0186061 A1    Jul. 23, 2009

(51) Int. Cl.
*A61F 2/00* (2006.01)
*A61K 9/16* (2006.01)
*A61K 9/00* (2006.01)

(52) U.S. Cl.
CPC ............ *A61K 9/1635* (2013.01); *A61K 9/0024* (2013.01); *A61K 9/0034* (2013.01)

(58) Field of Classification Search
USPC .......................................... 424/400, 422, 423
See application file for complete search history.

(56) References Cited

U.S. PATENT DOCUMENTS

| | | | | |
|---|---|---|---|---|
| 2,290,600 A | * | 7/1942 | Neher et al. | 525/60 |
| 2005/0256468 A1 | * | 11/2005 | Qin et al. | 604/358 |
| 2005/0287180 A1 | * | 12/2005 | Chen | 424/400 |
| 2012/0177697 A1 | * | 7/2012 | Chen | 424/400 |

FOREIGN PATENT DOCUMENTS

| | | | |
|---|---|---|---|
| EP | 0499164 | * | 8/1992 |
| WO | WO 01/70289 | * | 9/2001 |

OTHER PUBLICATIONS

Harris et al., Nature Reviews/Drug Discovery, vol. 2, 214-221, Mar. 2003.*

* cited by examiner

*Primary Examiner* — Michael G Hartley
*Assistant Examiner* — Robert Cabral
(74) *Attorney, Agent, or Firm* — The Marbury Law Group, PLLC

(57) ABSTRACT

The present invention relates to an injectable composition which comprises polymeric, water-insoluble, non-biodegradable, anionic particles, these particles having an irregular shape and a biocompatible carrier with a lubricated surface, a method for preparing the same, a method for treating a tissue in a patient which comprises injecting into the tissue site the injectable composition as a permanent implant and the use of the injectable composition as a medicament, particularly for bulking a tissue site.

17 Claims, No Drawings

COMPOSITION COMPRISING POLYMERIC, WATER-INSOLUBLE, ANIONIC PARTICLES, PROCESSES AND USES

BACKGROUND OF THE INVENTION

The present invention relates to the permanent augmentation of soft tissues and, more particularly to the treatment of urological disorders, e.g., urinary incontinence, and vesicoureteral reflux, by endoscopic injection of biocompatible anionic microparticles into submucosal tissues.

Since this invention is closely related to the treatment of incontinence, it will be described in detail by reference thereto.

For a simple explanation, incontinence occurs when the resistance to urine flow has decreased excessively, i.e., urethral resistance to urine outflow has, from whatever cause, been lowered to the point when it can no longer resist increased intra-abdominal pressure.

Urinary incontinence is a usual problem that affects people of different ages. This pathology predisposes a patient to urinary tract infections and urosepsis among others.

Urinary incontinence is also associated with social and psychological problems, as people affected with urinary incontinence show depression and social stigmatization.

One of the treatments actually proposed to solve urinary incontinence is the injection of biocompatible polymeric materials in the internal tissue e.g., in the urethra, in order to augment the soft tissue and restore continence.

Many of the biocompatible materials that have been used for augmenting the soft tissues e.g. are collagen, gelatin, and especially one of the most biocompatible molecules: hyaluronic acid. Beads of these natural crosslinked polymers are also currently used. However, all of those polymers were also biodegradable.

More recently, the biomaterials used in the treatment of urinary incontinence are synthetic non-biodegradable polymers and hydrogel polymers such as silicone rubber, polytetrafluoroethylene, polyacrylonitrile-polyacrylamide, and polyacrilates. Moreover, those hydrogel polymers were loaded with biological biodegradable polymers or autologous cells.

Most often, the biomaterials and their biocompatible carriers are delivered to the tissue by injection with an appropriate syringe.

The use of various injectable polymeric materials to treat urinary incontinence through the augmentation of tissues is known in the art.

Related to the use of biocompatible, biodegradable polymers for tissue augmentation, U.S. Pat. No. 5,143,724 describes the use of viscoelastic polymers with high biocompatibility like hyaluronic acid or crosslinked hyaluronans. Those highly anionic materials show very low cell interaction, they are often used in cosmetic surgery, but they have limited use in tissue augmentation due to the fact that hyaluronic acid will spread out of the tissues and also because hyaluronic acid is degraded.

Another biocompatible biodegradable biopolymer used in the treatment of urinary incontinence is collagen protein. U.S. Pat. No. 4,837,285 to Berg et al., relates to a collagen-based composition for augmenting soft tissue. The inventors describe the use of resorbable matrix beads of collagen with an average pore size of about 50 to 350 µm. Berman C. J. et al., Journal of Urology. 1997, 157; 122-124), describe the use of crosslinked collagen in the treatment of urinary incontinence following radical prostatectomy. However, the use of collagen shows contradictory results. A study of McCell. M, and Delustro, F., published in 1996 in Journal of Urology 155, 2068-2973 suggests the possible sensitization in patients because specific IgG and IgA antibodies appear after injection of bovine collagen.

Non-biodegradable polymers were used, e.g., injection of polytetrafluoroethylene (PTFE) in the past was used to treat urinary incontinence, see Kaufman et al., "Transurethral polytetrafluoroethylene injection for post-prostatectomy Urinary incontinence" 1984—Journal of Urology .132, p 463-464.

However, the presence of very small PTFE particles in the formulations was a problem since undesirable particle migration and serious granulomatous reaction take place. One commercial product containing PTFE particles with a diameter lower than 30 µm suspended in glycerin is available under name Polytef® (trademark of Mentor Corp. of California).

In order to overcome the problem of the migration, it has been proposed to use polymer particles of larger size.

In U.S. Pat. No. 5,336,263, the use of microparticles of silicone (polysiloxane and dimethylsiloxanes), with an average particle size in the range of from about 100 to 600 µm, is described as a method for long-term treatment of urinary incontinence.

EP Patent application No. 636014, U.S. Pat No. 5,258,028, and U.S. Pat No. 5,336,263 describe the use of textured microparticles of silicone in the manufacture of a composition for the long term treatment of urological disorders, such as incontinence. The aforementioned microparticles are dispersed in a physiologically biocompatible carrier and have an average size between 80 and 600 µm. The composition can be injected through a hypodermic needle.

French Patent number 2 836 921 A1 also describes tissue bulking made of silicone. The inventors describe injectable foam particles with biocompatible characteristics that are suspended in a biocompatible carrier, in which most of said particles have a diameter between 100 and 2000 µm. The silicone foam particles used to treat urinary incontinence have a reversible compression capacity between 300 and 420%.

The other compositions mentioned in the treatment of urinary incontinence are described as non-biodegradable water insoluble polymers denominated hydrogel.

EP 402,031 relates to an injectable composition, comprising a plurality of polymeric discrete particles, physiologically compatible, non-biodegradable, and of an average diameter ranging between 0.27 and 5.08 mm, and having a lubricated surface. These microparticles are deformable in a reversible manner, in approximately 20 to 75% of their external diameter. This composition contains microparticles of polyacrylonitrile in regular shape: in the form of spheres or macrodiscs.

U.S. Pat No. 6,335,028 "Implantable particles for urinary incontinence" describes an injectable composition for the treatment of urinary incontinence, gastroesophageal reflux disease and amelioration of skin wrinkles, using a biocompatible hydrophilic cationic copolymer composed by acrylic monomer and cationic monomer. The spherical particles can be loaded with different therapeutic agents such as antidiuretic, anti-inflammatories, cell adhesion promoter etc., and also with autologous cells. The spherical microparticles have a diameter ranging between 10 to 1000 microns.

U.S. Published Patent Application 2002/0068089 describes a method for treating gastroesophageal reflux disease by injection of a bulking agent. This composition also contains cationic biocompatible hydrophilic microparticles that can be loaded with different therapeutic agents, including autologous cells. Those cationic particles have a diameter ranging between 10 to 1000 microns.

WO 0170289 "Injectable and swellable microspheres for tissue bulking" relates to injectable compositions comprising substantially spherical microspheres used for tissue bulking in the treatment of urinary incontinence, urinary reflux disease and gastro-esophageal reflux disease. The microspheres are hydrophilic, biocompatible, swellable polymers like acrylic polymers, starch-acrylonitrile polymers and also polyethylene oxide among others. This composition comprising microspheres also comprises an amount of 10 to 90% of biocompatible saline carrier that contain acylamino-e-propion-amido-3-triiodo-2,4,6-benzoic acid (a contrast agent) and the microspheres have the property to swell about 1 to 4 times their average diameter after injection in the tissues. The microspheres may also be chemically modified with different biological molecules with therapeutic properties. These microspheres may be associated with autologous cells.

From this state of the art, it appears that in recent years, many approaches and treatments have been proposed to cure or relieve urinary incontinence by injection. While some of these approaches have enjoyed relative success, relief has been, for the most part, only temporary in those patients where success is noted. Thus, there remains a very important need for a treatment that will provide a lasting remedy for successful treatment of such urological disorders.

SUMMARY OF THE INVENTION

The present application discloses an invention that seeks to provide a long lasting, safe, effective treatment of tissue bulking. This problem has been solved by using an injectable composition comprising a discrete population of highly anionic, polymeric particles, having an irregular shape and a biocompatible carrier with a lubricated surface.

Advantageously, this composition allows improvement in the treatments of urological disorders such as urinary incontinence and urinary reflux disease.

A first object of the present invention is to provide an injectable composition comprising polymeric, water-insoluble, non-biodegradable, anionic particles, these particles having an irregular shape and a biocompatible carrier with a lubricated surface wherein the composition is injectable through needles of about 16 to 30 gauge.

A second object of the present invention is to provide a method for preparing the injectable composition by mixing polymeric, water-insoluble, water swellable, non-biodegradable, anionic particles of irregular shape and a biocompatible carrier with a lubricated surface.

A third object of the present invention is to provide a method for treating tissues in a patient, this method comprising injecting into the tissue site the injectable composition according to the invention, particularly this method consisting of bulking the tissue site.

Other objects, advantages, features of the present invention are explained in the following description and examples.

SPECIFIC DESCRIPTION OF THE PREFERRED EMBODIMENTS

The polymeric particles used in the composition of the present application are water-insoluble, meaning they cannot dissolve in water. These particles are not swellable in conventional conditions.

These polymeric particles are non-biodegradable, meaning they are not absorbed by the body, but these particles are biocompatible.

The injectable composition of particles is subjected to different and exhaustive treatments with different organic solvents and aqueous solvents that include high alkaline pH (pH 12) and high ionic strength (3M NaCl) to remove all the hydrophobic and hydrophilic impurities in order to obtain an injectable composition with physiologically-biocompatible properties.

To be considered as an injectable physiologically-biocompatible composition, the composition must be subjected to a series of tests that must be approved successfully. The composition of this invention was considered physiologically-biocompatible after approval of the following tests:

a—A test of genotoxicity by reverse mutation, developed in *Salmonella Thyphimurium*, known as the AMES test, made under ISO 10993-3 norms.
b—A cytotoxicity test, according ISO 10993-5.
c—A test for bacterial endotoxins according to USP XXIII.
d—Local limphatic ganglia sensitization assay (LLNA), according to ISO 10993-10.
e—Subcutaneous and urethral implantation test in rabbits, according to ISO 10993-6.
f—A migration test at 13 weeks and 12 months.
g—A bone marrow micronucleus assay developed in rats according ISO 10993-3.
h—Chromosomal aberrations in mammal cells, study according to ISO 10993-3.
i—Biodegradation test pre-implant and post-implant according ISO 10993-13.
j—Chemical Characterization of materials according ISO 10993-18.

The polymeric particles are anionic, meaning they possess a highly electronegative surface. Polymeric particles with anionic surface were chosen to reduce or minimize the binding of particles to peripheral cell tissue and thus avoiding side effects in cell function.

After injection, these anionic polymeric particles are coated with a fine fibrotic growth which appears within a few days, this fine fibrotic growth stabilizing the particles in the tissue site where they have been injected, resulting in a stable bulking effect of the treated tissue.

In a preferred embodiment, in the injectable composition according to the present invention, the polymeric particles represent from 0.5 to 10%, preferably from 3 to 5% by weight of the injectable composition.

In a preferred embodiment, in the injectable composition according to the present invention, the biocompatible carrier represents from 90 to 99.5%, preferably from 95 to 99.5% by weight of the injectable composition.

Particularly the polymeric particles are chosen from anionic particles of:
  the complex of crosslinked sodium polyacrylate polymer with a copolymer of polyvinyl alcohol-polyvinyl acetate, being the copolymer of polyvinyl alcohol-polyvinyl acetate grafted onto the backbone of polyacrylate chain, preferably the copolymer of polyvinyl alcohol-polyvinyl acetate has a hydrolysis degree between 75 and 90%, and a molecular weight (MW) comprised in the range 25-100 kDa;
  the pegylated forms of this complex of crosslinked sodium polyacrylate polymer with a copolymer of polyvinyl alcohol-polyvinyl acetate;
  particles of crosslinked sodium polyacrylate polymer;
  the pegylated forms of this crosslinked sodium polyacrylate polymer;
  mixtures thereof.

Preferably, the complex of crosslinked sodium polyacrylate polymer with a copolymer of polyvinyl alcohol-polyvinyl acetate has a molecular weight comprised in the range 7000-13000 kDa, more preferably comprised in the range 9000-11000 kDa, particularly around 10000 kDa and the copolymer polyvinyl alcohol-polyvinyl acetate has a molecular weight comprised in the range 25-100 kDa, preferably comprised in the range 25-35 kDa, particularly around 30 kDa. Before preparing the composition, the particles are subjected to different purification steps, that include successive treatments with organic solvents to remove hydrophobic impurities and highly saline and alkaline treatments to remove hydrophilic impurities in order to obtain physiologically-biocompatible properties. The purified irregular dry particles show an average of high size diameter from 150 to 800 microns before swelling.

The anionic microparticles used in this composition are swelled with a biocompatible carrier to obtain a gel structure with a lubricated surface.

The carrier is added to the particles in such a way that the carrier is fully absorbed, given a composition with a semi-dried gelled structure. The anionic particles of this composition swelled with the biocompatible carrier in the condition described above: the composition according to the invention is in the form of swelled hydrogel particles having preferably a diameter range from 0.6 to 3 mm.

In a preferred embodiment of the present invention, the biocompatible carrier is a carrier free of pyrogenic substances, for example, a hydro organic solution free of pyrogenic substances (e.g.: the carrier contains water (60%) and 40% of some organic molecule such as glycerol or PEG).

Preferably the pH of the carrier is approximately 6.

In a first embodiment, the biocompatible carrier is glycerol in a concentration from 15 to 60%, preferably from 30 to 50% in distilled water or isotonic saline solution.

In a second embodiment, the biocompatible carrier is polyethyleneglycol in a concentration from 15 to 60%, preferably from 35 to 50% in distilled water or isotonic saline solution.

In a third embodiment, the biocompatible carrier is polyethyleneglycol with a molecular weight from 200 to 1000 Daltons.

In a preferred embodiment of the present invention, the purified anionic particles of this composition are partially compressible, deformable under pressure. This property makes these particles able to be injected (injectable) through needles of about 16 to 30 gauge.

In a first embodiment, the swelled hydrogel particles, after passed through a 23-gauge needle, are in the range from 10 to 1200 microns, preferably around 300 microns.

In a second embodiment, 85 to 95% of the swelled hydrogel particles, after passed through a trans-urethral catheter of 33 cm with a 23-gauge needle, are in the range from 100 to 1200 microns.

In a third embodiment, at least 30% of the swelled hydrogel particles, after passed through a trans-urethral catheter of 33 cm with a 23-gauge needle, are in the range from 400 to 1200 microns.

The present invention also comprises a method for preparing the injectable composition by mixing polymeric, water-insoluble, water swellable, non-biodegradable, anionic particles of irregular shape and a biocompatible carrier with a lubricated surface.

Preferably, the injectable composition according to the invention is prepared with polymeric particles chosen from particles of the complex of crosslinked sodium polyacrylate polymer with a copolymer of polyvinyl alcohol-polyvinyl acetate in a pegylated form and of the crosslinked sodium polyacrylate polymer in a pegylated form wherein the pegylation specifically occurs on the carboxylic groups of the polymers.

More preferably, the pegylation of the carboxylic groups takes place by addition of PEG-hydrazide, an activated form of polyethylenglycol where the hydrazide group allow carboxyl pegylation selectively in presence of N,N'-dicyclohexylcarbodiimide (DCC), or in presence of a water soluble coupling agent such as N-(-3 dimethylaminopropyl)-N'-ethylcarbodiimide hydrochloride (EDC).

Particularly, the pegylated polymer contains from 1% to 90% of the carboxylic groups of the total of carboxylic groups in pegylated form.

Particularly, the molecular weights of polyethylenglycol and of PEG-hydrazide are in the range between 1K and 30K.

The in vivo studies dealing with injection of these anionic microparticles show that little or no change in the bulk size takes place after injection, thus demonstrating that this composition does not swell after implantation in tissues.

In a preferred embodiment of the present invention, these anionic particles are not capable of being hydrolyzed or removed from the site of injection by elements of the immune system like macrophage cells, or by the lymphatic system.

The present invention also provides a kit for tissue bulking where the injectable composition is ready to use in a prefilled syringe and a method to sterilize it. The anionic microparticles swelled with biocompatible carrier to obtain a semi-dry gelled structure were loaded into a 1 ml syringe in which the needle was replaced by a removable cap of silicone. The syringe containing the composition was sealed into a double pouch bag and sterilized by heating between 121° C. to 132° C. during 20 to 30 minutes.

The third object of the present invention is a method for treating tissues in a patient, this method comprising injecting into the tissue site the injectable composition according to the invention as a permanent implant, particularly this method consists in bulking the tissue site.

In a first embodiment, this method consists of augmenting the tissue deficiency or replacing the tissue in the treatment of degenerative diseases.

In a second embodiment, this method is for the purpose of treatment of urinary incontinence, urinary reflux disease, vesico-urethral fistula, fecal incontinence and gastroesophageal reflux disease.

In a third embodiment, this method is for the purpose of reconstruction of parts of the body such as breasts, buttocks, lips, scars.

In a fourth embodiment, this method is for the purpose of treatment of arthritis and arthrosis in mammals.

The fourth object of the present invention is to provide an injectable composition according to the present invention as a medicament, particularly used for the manufacture of a medicament for bulking a tissue site.

In a first embodiment, the injectable composition is used for the manufacture of a medicament for augmenting tissue deficiency or replacing the tissue in the treatment of degenerative diseases.

In a second embodiment, the injectable composition is used for the manufacture of a medicament for the treatment of urinary incontinence, urinary reflux disease, vesico-urethral fistula, fecal incontinence and gastroesophageal reflux disease.

In a third embodiment, the injectable composition is used for the manufacture of a medicament for the reconstruction of parts of the body such as breasts, buttocks, lips, scars.

In a fourth embodiment, the injectable composition is used for the manufacture of a medicament for the treatment of arthritis and arthrosis in mammals.

Reports of clinical treatments indicate that particles less than about 60 μm of diameter can be engulfed by macrophages and transported to lymph nodes. Particles greater than 60 µm, however, have not been observed within the cell or within lymph nodes. It has been mentioned that particles with diameters higher than 80 µm appear safe from initiating such body reactions.

According to R. Dmochowski (Bulking agents make resurgence in use for urinary incontinence, The BBI Newsletter, July 2002, pp 191), the size of particles must be higher than 100 µm or instigate adhesion to host tissue.

According to the present invention, the size of the particles swelled at 4% (p/v) with biocompatible carrier after extrusion through a catheter of 33 cm containing at the end a 23 gauge needle shows a high size diameter averaging between 250 µm to 350 µm and preferably around 300 µm.

From data of the granulometric analyses of particles size, it was observed that 30% of particles have a size above 400 µm (85% to 95% have a size greater than 100 µm). Taken together, these results demonstrate, on the one hand, the elasticity and deformability of the particles and, on the other hand, that the microparticles used according to the invention are not capable of being hydrolyzed or eliminated by elements of the immune system like macrophage cells, or by the lymphatic system.

The non-biodegradable microparticles of this composition are also thermally stable which allows one to heat the preparation between 121° C. to 132° C. during 20 to 30 minutes, this heating treatment being known as sterilization by autoclaving.

The in vivo studies consisting of injecting this composition of semi-dried amorphous hydrogel particles in different tissues shows that the bulk practically does not swell even after 3 months (after injection).

Without wishing to be bound to a theory, the absence of swelling of the composition according to the invention may be explained by at least two different ways:
- the injection of this composition into tissues, e.g. urethral walls, avoids contact of the microparticles with fluids, and
- after 24 or 48 hours, the microparticle bulk was found to be coated by a layer of fibrin, which finally was transformed in a thin layer of fibrotic growth. This coating may act as a rigid basket maintaining together the bulk of injected microparticles in its initial size.

In conclusion, the application of this permanent implant in the treatment of urinary diseases reveals these advantages:

1—The composition comprising the anionic irregular microparticles passes through a gauge needle, the microparticles clump together in a continuous jelly stable structure with a lubricious surface which is easy to inject.

2—The jelly structure of the microparticles may be injected through a 16-30 gauge needle.

3—The highly electronegative surface of this composition avoids direct binding with tissue cells, consequently the potential side effects of its interaction with those cells is avoided.

4—The composition shows a stable tissue bulking that remains essentially unalterable with time because: the high size of particles cannot be affected by the immune or lymphatic system and the injected material is coated with a natural fibrotic growth.

EXAMPLES

Example 1

Purification of Anionic Microparticles

In order to assess the physiologically-biocompatible properties of the anionic microparticles, a process is described by which the amorphous polymeric particles are treated in different steps with organic and aqueous solvents in order to remove hydrophobic and hydrophilic impurities.

1—To a sample of 10 g of dry anionic microparticles of the complex of crosslinked sodium polyacrylate polymer, a copolymer of polyvinyl alcohol-polyvinyl acetate 200 ml of chloroform was added and the mixture was incubated at 45° C. under continuous stirring during 2 hours. Then the chloroform was discarded, and the procedure was repeated three times.

2—In the next step, the microparticles were treated with 200 ml of chloroform-ethanol (2:1 vol/vol) in similar conditions as described for chloroform alone.

3—The microparticles were treated with 200 ml of ethanol under similar conditions as described above.

4—The particles were treated three times with 200 ml of dimethylsulfoxide (DMSO) at 45° C. during 2 hours each.
These procedures were done to assure removal of the hydrophobic impurities.

5—To remove the hydrophilic impurities, the particles were incubated with 500 ml of a solution containing 3 M NaCl and 0.2 M NaHO, during 6 to 12 hours at a temperature from 4 to 20° C.

6—The particles were washed at least 14 times with 5 liters of tri-distillated water to remove the salt and reach a pH that ranged between 6 and 7.

7—To dry the purified amorphous particles, successive additions of ethanol, and acetone were made and finally the sample was heated to 70° C. for at least 6 hours to dryness.

Example 2

Preparation of Injectable Suspension of Anionic and Amorphous Microparticles The dry particles (10 g) purified as described in Example 1 were re-suspended with 500 ml of the sterile biocompatible carrier composed of glycerol-sodium chlorate (30-70 vol/vol). The suspension of particles was gently mixed during 15 minutes to obtain an homogeneous distribution of the carrier. The sample was allowed to stand for 24 hours and then loaded on the 1 ml syringe and the top was sealed with a silicon cap. Finally, the syringes were sterilized by heating between 121° C. to 132° C. for 20 to 30 min.

Example 3

Injection of Crosslinked Sodium Polyacrylate Polymers, for In Vivo Bulking

Two year old female dogs were used in the assays, and they were anesthetized with alothane.

To implant the microparticles in the urethral wall, an endoscopy of 20 Fr with an optic of 30 degrees was used. In order to make the injection, a "William cystoscopic injection needle—Cook" was used with a 5 Fr and 35 cm long catheter and a 23 gauge needle.

Before starting the procedure, the animal vagina was washed with an antiseptic solution of povidone. To facilitate the access in urethral conducts and avoid mucosal lesions, a 2% xilocaine gel was used. The endoscope was introduced to reach the bladder, and the bladder neck and uretheral conduits were controlled. At 1 cm of the neck of the bladder, the 23 gauge needle was pushed and inserted into the urethral wall. The samples were injected at hours 3, 6 and 9 with a sample volume to completely close the urethral conduit. To avoid material leaving the injection site, the needle was allowed to stay in place for 20 seconds. After the injection of the microparticles, the endoscope must not be reintroduced into the bladder to avoid the flattening of the bulks.

Endoscopic observations and ecography analysis to 3, 6, 9 and 12 months were used to evaluate the bulking agent treatment. The post-images of the implant show a substantial reduction in the lumen of the urethra. The endoscopic observations and the ecography showed that the microparticle bulks stayed stable during time of the study (12 months).

The volume of the injected microparticles did not present significant changes.

The anatomopathological studies of the injected tissue shows:

1) No foreing body reactions, inflammation or infections were seen.

2) 48 hours after injection, a thin fibrotic tissue appeared on the particles, covering the injected particles and protecting them from migration from the urether to other tissues.

3) No particles were observed 12 months after injection, in the anatomopathological study. After a very complete observation of all the organs (heart, urethra, lungs, liver, intestine, kidneys, glandula suprarrenalis, spleen, lymph node, pancreas, encephalon, ovary, oviduct, uterus), no dangerous migrations were observed.

The invention claimed is:

1. An injectable composition comprising:
   (a) polymeric, water-insoluble, non-biodegradable, anionic particles having irregular shapes,
      wherein the polymeric particles are present in the injectable composition in an amount ranging from 0.5% to less than 5% by weight, relative to the total weight of the injectable composition;
      wherein the polymeric particles comprise particles having a size ranging from 150 to 800 microns,
      wherein the polymeric particles are chosen from:
         (1) particles of a complex of crosslinked sodium polyacrylate polymer with a copolymer of polyvinyl alcohol-polyvinyl acetate;
         (2) pegylated forms of the complex of crosslinked sodium polyacrylate polymer with a copolymer of polyvinyl alcohol-polyvinyl acetate;
         (3) combinations thereof; and
         (4) mixtures thereof with particles of pegylated forms of crosslinked sodium polyacrylate polymer; and
      wherein the complex of crosslinked sodium polyacrylate polymer with a copolymer of polyvinyl alcohol-polyvinyl acetate has a molecular weight ranging from 7000 to 13000 kDa, the copolymer polyvinyl alcohol-polyvinyl acetate having a molecular weight ranging from 25 to 100 kDa;
      and
   (b) a biocompatible carrier with lubricating properties, chosen from glycerol in a concentration ranging from 15% to 60% in distilled water or isotonic saline solution;
      wherein the biocompatible carrier is present in the injectable composition in an amount ranging from 95% to 99.5% by weight, relative to the total weight of the injectable composition,
      wherein the injectable composition is in the form of swelled hydrogel particles having a diameter ranging from 0.6 to 3.0 mm, and
      wherein the injectable composition is injectable through needles of about 16 to 30 gauge.

2. An injectable composition according to claim 1, wherein the biocompatible carrier is free of pyrogenic substances.

3. An injectable composition according to claim 2, wherein the biocompatible carrier is a hydro organic solution free of pyrogenic substances.

4. An injectable composition according to claim 1, wherein the swelled hydrogel particles pass through an opening of a 23-gauge needle, and when passing through said opening, at least 85 to 95% of the swelled hydrogel particles have a diameter reduced to a value ranging from 10 to 1200 microns.

5. An injectable composition according to claim 1, wherein the swelled hydrogel particles pass through an opening of a trans-uretheral catheter of 33 cm with a 23-gauge needle, and after passing through said opening at least 30% of the swelled hydrogel particles have a diameter reduced to a value ranging from 400 to 1200 microns.

6. An injectable composition according to claim 1, further comprising a medicament.

7. Method for preparing the injectable composition according to claim 1, including the step of mixing the polymeric, water swellable, water-insoluble, non-biodegradable, anionic particles of irregular shape and the biocompatible carrier with a lubricated surface.

8. Method for preparing the injectable composition according to claim 7, wherein the polymeric particles are chosen from the group consisting of (1) particles of a complex of crosslinked sodium polyacrylate polymer with a copolymer of polyvinyl alcohol-polyvinyl acetate in a pegylated form, and (2) of the crosslinked sodium polyacrylate polymer in a pegylated form wherein the pegylation specifically occurs on the carboxylic groups of the polymers.

9. Method for preparing the injectable composition according to claim 8, wherein the pegylation of the carboxylic groups takes place by addition of PEG-hydrazide, an activated form of polyethylenglycol where the hydrazide group allows carboxyl pegylation selectively in presence of N,N'-dicyclohexylcarbodiimide (DCC), or in presence of a water soluble coupling agent such as N-(-3 dimethylaminopropyl)-N'-ethylcarbodiimide hydrochloride (EDC).

10. Method for preparing the injectable composition according to claim 8, wherein the pegylated polymer contains from 1% to 90% of the carboxylic groups of the total of carboxylic groups in pegylated form.

11. Method for preparing the injectable composition according to claim 9, wherein the molecular weight of polyethylenglycol and of PEG-hydrazide are in the range between 1K and 30K.

12. Method for treating a tissue in patient which comprises injecting into the tissue site the injectable composition as a permanent implant according to claim 1.

13. Method for treating a tissue in a patient according to claim 12, wherein the treatment consists of bulking of the tissue site.

14. Method for treating a tissue in a patient according to claim 13, wherein the treatment consists of augmenting tissue deficiency or replacing tissue in the treatment of degenerative disease.

15. Method according to claim 12 for treatment of urinary incontinence, urinary reflux disease, vesicourethral fistula, fecal incontinence or gastroesophageal reflux disease.

16. Method according to claim 12 for reconstruction of parts of a body chosen from the group consisting of breasts, buttocks, lips, and scars.

17. Method according to claim 12 for treatment of arthritis and arthrosis in mammals.

* * * * *